(12) United States Patent
Hinz et al.

(10) Patent No.: US 9,534,092 B2
(45) Date of Patent: Jan. 3, 2017

(54) PURIFICATION SYSTEMS AND METHODS

(75) Inventors: Wolfgang Hinz, Killingworth, CT (US); Ryan Jones, New Haven, CT (US); David Light, New Haven, CT (US)

(73) Assignee: Life Technologies Corporation, Carlsbad, CA (US)

(*) Notice: Subject to any disclaimer, the term of this patent is extended or adjusted under 35 U.S.C. 154(b) by 1334 days.

(21) Appl. No.: 13/371,264

(22) Filed: Feb. 10, 2012

(65) Prior Publication Data
US 2012/0205294 A1 Aug. 16, 2012

Related U.S. Application Data

(60) Provisional application No. 61/441,497, filed on Feb. 10, 2011, provisional application No. 61/473,232, filed on Apr. 8, 2011.

(51) Int. Cl.
| | | |
|---|---|---|
| *B07B 1/00* | (2006.01) | |
| *C08J 3/12* | (2006.01) | |
| *C12N 15/10* | (2006.01) | |

(52) U.S. Cl.
CPC ............. *C08J 3/12* (2013.01); *C12N 15/1017* (2013.01); *C08J 2300/14* (2013.01)

(58) Field of Classification Search
None
See application file for complete search history.

(56) References Cited

U.S. PATENT DOCUMENTS

| | | | | |
|---|---|---|---|---|
| 4,794,166 A | * | 12/1988 | Engelhardt | C08F 6/003 523/315 |
| 5,468,847 A | * | 11/1995 | Heilmann et al. | 530/413 |
| 5,948,441 A | * | 9/1999 | Lenk | A61K 9/1277 264/4.1 |
| 2002/0034525 A1 | * | 3/2002 | Sakai et al. | 424/401 |
| 2009/0166291 A1 | * | 7/2009 | Jackson | 210/641 |
| 2009/0318309 A1 | | 12/2009 | Kimble et al. | |
| 2010/0101997 A1 | * | 4/2010 | Tateishi | 210/636 |
| 2010/0136544 A1 | | 6/2010 | Agresti et al. | |
| 2010/0137143 A1 | | 6/2010 | Rothberg et al. | |

(Continued)

FOREIGN PATENT DOCUMENTS

| | | | |
|---|---|---|---|
| WO | WO 2008123099 A1 * | 10/2008 | ........... B01D 61/027 |
| WO | 2008133571 | 11/2008 | |

(Continued)

OTHER PUBLICATIONS

Ivnitsky et al., "Characterization of membrane biofouling in nanofiltration processes of wastewater treatment," Mar. 10, 2005. Desalination 185 (2005) 255-268.*

(Continued)

*Primary Examiner* — Michael H Wilson
*Assistant Examiner* — Katherine Will

(57) ABSTRACT

A method of preparing hydrogel particles includes applying a solution including a plurality of hydrogel particles to a stir cell. A retentate side of a filter defines a lower surface of the stir cell. The filter has the retentate side and a permeate side. The method further includes, while stirring the solution within the stir cell, dispensing a buffer solution at a first flow rate to the stir cell and drawing a permeate from the permeate side of the filter using a pump at a second flow rate, the permeate including a subset of the plurality of hydrogel particles.

9 Claims, 8 Drawing Sheets

(56) References Cited

U.S. PATENT DOCUMENTS

2010/0301398 A1    12/2010  Rothberg et al.
2010/0304982 A1    12/2010  Hinz et al.
2011/0129941 A1*    6/2011  Kumacheva .......... B01F 3/0807
                                                                436/180

FOREIGN PATENT DOCUMENTS

WO       2009015290      1/2009
WO       2010002455      1/2010
WO       2010/138187    12/2010

OTHER PUBLICATIONS

PCT/US2012/024756, International Search Report and Written Opinion mailed Jul. 25, 2012.
U.S. Appl. No. 61/263,734, filed Nov. 23, 2009.
U.S. Appl. No. 61/291,788, filed Dec. 31, 2009.
U.S. Appl. No. 61/297,203, filed Jan. 21, 2010.
International Preliminary Report on Patentability for International Application No. PCT/US2012/024756 mailed Aug. 13, 2013, 5 pages.

* cited by examiner

PURIFICATION SYSTEMS AND METHODS

CROSS-REFERENCE TO RELATED APPLICATION(S)

This application claims benefit of U.S. Provisional Application No. 61/441,497, titled "PURIFICATION METHODS, COMPOSITIONS, SYSTEMS, APPARATUSES AND KITS," filed Feb. 10, 2011, which is incorporated herein by reference in its entirety.

This application claims benefit of U.S. Provisional Application No. 61/473,232, titled "PURIFICATION SYSTEMS AND METHODS," filed Apr. 8, 2011, which is incorporated herein by reference in its entirety.

FIELD OF THE DISCLOSURE

The disclosure, in general, relates to purification methods and system for purification.

BACKGROUND

Polymeric particles are increasingly being used as components in separation techniques and to assist with detecting analytes in both chemical and biological systems. For example, polymeric particles have been used in chromatographic techniques to separate target molecules from a solution. In another example, polymeric particles having a magnetic coating are utilized in magnetic separation techniques. More recently, polymeric particles have been used to enhance ELISA-type techniques and can be used to capture polynucleotides.

Nevertheless, such separation and analytical techniques have suffered as a result of variance in particle size. Large variance in particle size leads to variance in particle weight, as well as variance in the number of reaction sites available for interacting with target analytes. For magnetic separations techniques, variance in size can lead to low efficiency separations. For chromatographic techniques and various polynucleotide capture techniques, variance in size can lead to variance in the number of sites available for interacting with polynucleotides, leading to variance in capture or separation efficiency.

SUMMARY

In a first aspect, a method of preparing polymeric particles includes filtering a plurality of polymeric particles through a first filter having a pore size at a first permeate velocity to provide a first subset of polymeric particles; and filtering the first subset of polymeric particles through a second filter having the pore size at a second permeate velocity to provide a second subset of polymeric particles; wherein the first and second permeate velocities are different.

In a second aspect, a method of preparing polymeric particles includes filtering a plurality of polymeric particles through a first filter having a first pore size at a first permeate velocity to provide a first subset of polymeric particles having a first average particle size; and filtering the first subset of polymeric particles through a second filter having a second pore size at a second permeate velocity to provide a second subset of polymeric particles having a second average particle size greater than the first average particle size; wherein the first and second pore sizes are at least the second average particle size.

In a third aspect, a method of preparing hydrogel particles includes applying a solution including a plurality of hydrogel particles to a stir cell, a retentate side of a filter defining a lower surface of the stir cell, the filter having the retentate side and a permeate side; and while stirring the solution within the stir cell, drawing a permeate from the permeate side of the filter using a pump at a first flow rate, the permeate including a subset of the plurality of hydrogel particles.

In a fourth aspect, a method of preparing hydrogel particles includes applying a solution including a plurality of hydrogel particles to a first stir cell, a retentate side of a first filter defining a lower surface of the first stir cell, the first filter having the retentate side and a permeate side, the first filter having a first pore size; and while stirring the solution within the first stir cell, dispensing a first buffer solution at a first flow rate to the first stir cell; and drawing a permeate from the permeate side of the first filter using a first pump at a second flow rate, the permeate including a subset of the plurality of hydrogel particles; applying the permeate to a second stir cell, a retentate side of a second filter defining a lower surface of the second stir cell, the second filter having the retentate side and a permeate side, the second filter having a second pore size; and while stirring within the second stir cell, dispensing a second buffer solution at a third flow rate to the second stir cell; and drawing from the permeate side of the second filter using a second pump at a fourth flow rate; and collecting a second subset of hydrogel particles from the retentate side of the second filter after a period of time; wherein the first and second pore size are the same.

In a fifth aspect, a plurality of particles wherein a subset of the plurality of particles comprise hydrogel and the plurality of particles has a coefficient of variance of not greater than 5%, In a sixth aspect, a system includes a buffer container to store a buffer solution; a first stir cell including a first filter defining a lower surface of the first stir cell, the first filter having a first pore size, the buffer container in fluid communication with the first stir cell; and a first pump in fluid communication with a permeate side of the first filter; a second stir cell including a second filter defining a lower surface of the second stir cell, the second filter having a second pore size less than the first pore size; and a second pump in fluid communication with a permeate side of the second filter.

BRIEF DESCRIPTION OF THE DRAWINGS

The disclosure will be discussed in reference with the following exemplary and non-limiting drawings in which liked elements may be represented with like numbers.

DETAILED DESCRIPTION

In an exemplary embodiment, a population of hydrogel particles is filtered to provide a subpopulation of hydrogel particles having a desired average particle size and a low coefficient of variance. In a particular example, the population of particles is applied to a stir cell filtration system. A subset of the population of hydrogel particles is filtered through a first filter by the stir cell filtration system and applied into a second stir cell filtration system including a second filter. As a result, larger particles within the population are removed and fine particles within the population removed leading a desired subpopulation of hydrogel particles having the desired narrow size distribution and average particle size. In particular example, the first and second filters have approximately the same pore size and particle size selection is performed by varying the flowrate of a buffer solution or the velocity of a permeate across the filters. In particular, the filter pore size of the first and second filters can be greater than the desired average particle size of the subpopulation of hydrogel particles.

It has been discovered that polymeric particles, such as hydrogel particles, behave differently than conventional solid particles in filtration systems. A hydrogel is a polymer that can absorb at least 20% of its weight in water, such as at least 45%, at least 65%, at least 85%, at least 100%, at least 300%, at least 1000%, at least 1500% or even at least 2000% of its weight in water.

It has further been discovered that variations in filtration system structure and the velocity of a permeate through the filter system has an influence on particle size selectivity of the filter. Size selectivity is enhanced when the permeate is drawn though a filter with a pump on the down stream side of the filter. It has also been discovered that particles of fine size can be removed with filters having a pore size similar to or greater than the desired average particle size of particles within the retentate.

Figure 1:
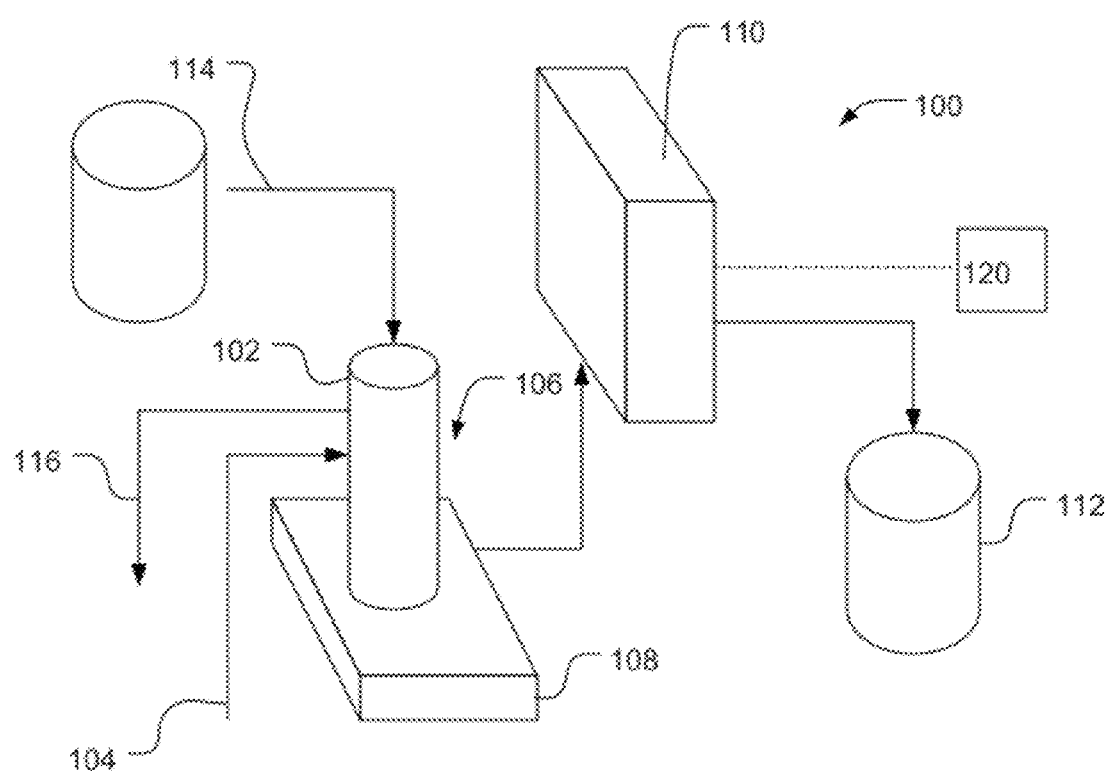
FIG. 1 illustrates a filtering system.

In particular, the filtration system includes a stir cell filter system and a pump. FIG. 1 illustrates a filtration system 100 including a filter 102 operable to receive a feed fluid 104. The feed fluid 104 may initially include polydispersed particles that are flexible, deformable, or compressible, such as hydrogel particles. The initial coefficient of variance of the fluid may be more than 35%. The coefficient of variance (CV) is defined as 100 times the standard deviation divided by average, where "average" is the mean particle diameter and standard deviation is the standard deviation in particle size. The "average" alternatively can be either the z-average or mode particle diameter. In accordance with usual practice, CV is calculated on the main mode, i.e., the main peak, thereby excluding minor peaks relating to aggregates. Thus, some particles below or above mode size may be discounted in the calculation which may, for example, be based on about 90% of total particle number of detectable particles. Such a determination of CV is performable on a CPS disc centrifuge or a coulter counter.

The filtration system 100 may include a stirring mechanism 106, as illustrated in FIG. 1. In an embodiment, the stiffing mechanism 106 may include a magnetic stirrer (not shown) on the upstream side of the filter 102 and a stir plate 108. The feed fluid 104 may be drawn across the filter 102 by a pump 110 that creates a negative pressure on the downstream side of the filter 102. In an embodiment, the pump 110 may be a syringe pump, as illustrated in FIG. 1. In other embodiments, a pump creating positive pressure on the upstream side may be used if measures are taken to mitigate variable compression.

In an embodiment, the pump 110 may be controlled by a controller 120 to maintain the flow rate through the filter 102 at a preset level. The measurement data of flow condition in the filtration system 100 may be fed back or forward to the controller 120, which uses the data to control the pump 110 and maintain the flow rate substantially constant regardless the change of flow conditions in the filtration system 100. The filtrate or permeate drawn by the pump 110 may be stored as in a storage container 112. The retentate retained by the filter 102 may be withdrawn via an outlet 116. In an example, as the concentration of the particles increases on the upstream side, a buffer feed 114 may be introduced to the filter 102 to improve the yield.

Depending on the volume of particles to be filtrated, a plurality of filtration systems 100 may be operating concurrently. In an example, the plurality of filtration systems 100 may be configured in a parallel arrangement. In another example, the feed fluid 104 of each filtration system 100 may be provided from a single source. In a further example, the output from each filtration system 100, such as the filtrate or the retentate may be stored in the same storage device 112.

In operation, the feed fluid 104 can be filtered through the filter 102 at a first flow rate, the filter 102 having a first pore size and a first size cutoff at the first flow rate, thereby producing a first retentate including a first plurality of particles having an average size that is greater than the first size cutoff, and a first filtrate or permeate. In an example in which deformable particles, such as hydrogel particles, are present in the feed fluid 104, an effective first flow rate may be within a range of 0.5 to 2.5 ml/min. In particular, the velocity, defined as the flow rate divided by the area of the filter, can be in a range of 0.025 cm/min to 0.17 cm/min, such as a range of 0.04 cm/min to 0.15 cm/min, a range of 0.05 cm/min to 0.14 cm/min. In an example, effective filtering of large deformable particles may be achieved with a flow rate of 1.5 ml/min over a 47 mm diameter filter.

After obtaining the first filtrate or permeate, the filtration system 100 optionally may be cleaned to remove the first retentate. The first filtrate may be filtered through the filter 102 again at a second flow rate, the filter 102 having a second size cutoff at the second flow rate, thereby producing a second retentate including a second plurality of particles having an average size that is greater than the second size cutoff, and a second filtrate including a third plurality of particles having an average size that is lesser than the second size cutoff.

In another example, the filtration system 100 may include a second filter substantially similar to the filter 102 for filtering the first filtrate at the second flow rate. The second retentate may be withdrawn through the outlet 116. In an embodiment in which deformable particles, such as hydrogel particles, are present in the first filtrate, an effective second flow rate may be within 0.25 to 2.0 ml/min across a filter having a 47 mm diameter. In particle, the permeate velocity can be in a range of 0.01 cm/min to 0.13 cm/min, such as a range of 0.02 cm/min to 0.11 cm/min. In an example, effective filtering of small deformable particles may be achieved with a flow rate of 1.0 ml/min across a filter having a diameter of 47 mm. Alternatively, the filters may have different pore size.

Figure 2:
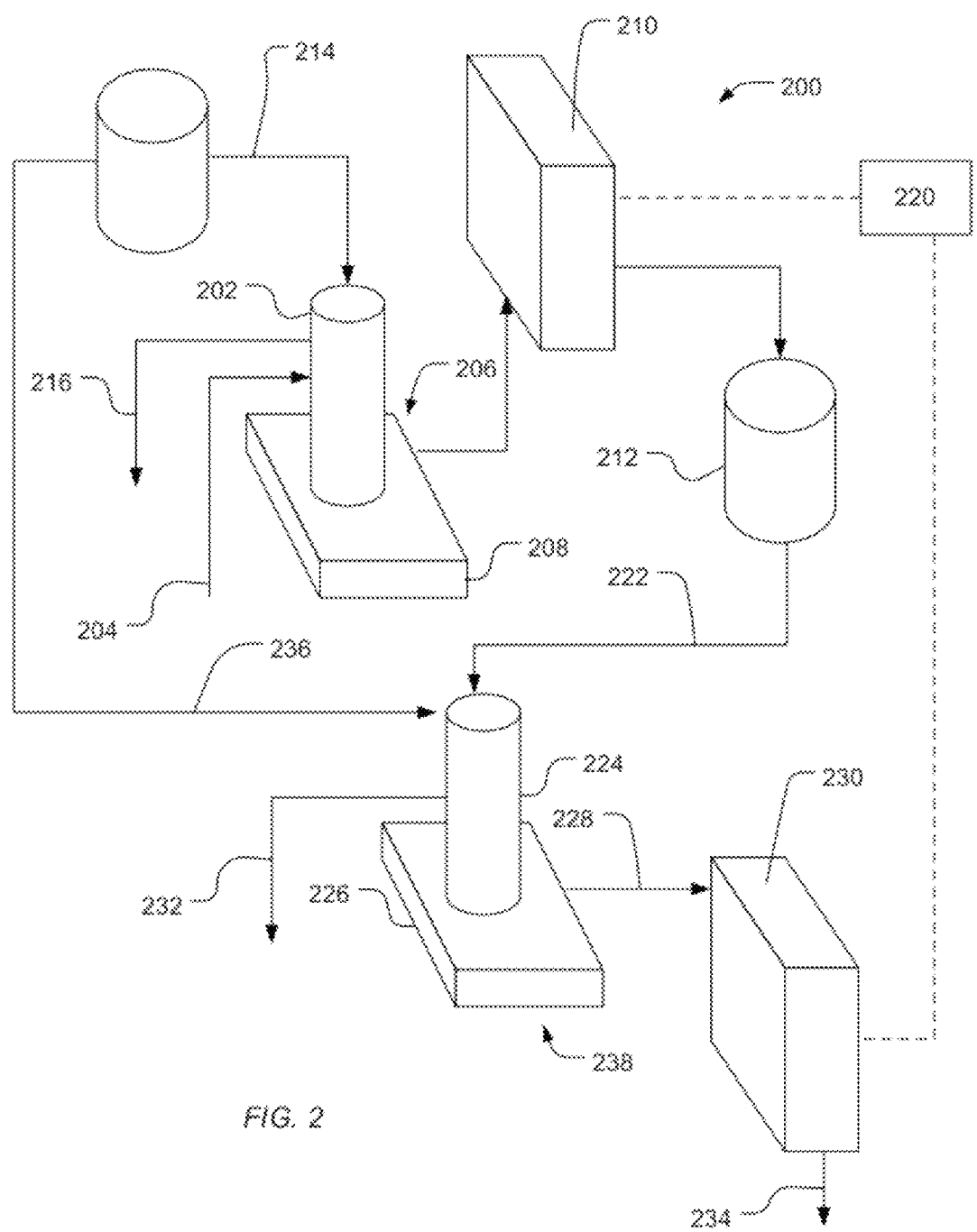
FIG. 2 illustrates another exemplary filtering system.

As illustrated in FIG. 2, a system 200 includes a first filtration system 202 and a second filtration system 224. The filtration system 202 is part of a stir cell filtration system 206 that includes a stir plate 208. The stir cell filtration system 206 is charged with the initial feed fluid 204. A buffer feed 214 is feed to the stir cell filtration system 206 and a permeate is drawn by the pump 210. At the end of the filtration cycle, the retentate is drawn through the outlet 216.

As illustrated, the stir cell filtration system 206 includes a retentate side of the filter, which is agitated, and a permeate side drawn by the pump 210. In an example, the pump 210 can be a syringe pump. Alternatively, the pump 210 can be selected from a variety of available pump types.

In the illustrated example, large particles are retained in the retentate and a separated subpopulation in the permeate can be transferred to the second filtration system 224, after optionally being stored at 212. Optionally, the permeate can be concentrated or diluted prior to a second filtration. At 222, the permeate subpopulation of hydrogel particles is to be fed to the second filtration system 224 to initiate a subsequent filtration cycle. The second filtration system 224 can be part of a stir cell filtration system 238 including a stir plate 226. While the permeate solution is stirred and the second permeate is drawn through the filtration system 224, a buffer solution 236 can be added to the stir cell filtration system 238. As illustrated, the buffer solution 236 is same buffer solution fed by buffer feed 214 to the first filtration system 202. Alternatively, the buffer solution fed to the second filtration system 224 can be different than the buffer solution fed to the first filtration system 202.

A second permeate 228 is drawn by a pump 230. The pump 230 can be a syringe pump. Alternatively, the pump 230 can be one of a variety of available pump types. In the illustrated example, the filtration system 224 separates particles of fine particle size from the desired retentate population. As such, the fine particles extracted with the second permeate 228 can be discarded at 234. After the filtration cycle, a retentate having the desired population of hydrogel particles can be withdrawn through the outlet 232.

A controller 220 can control one or both of the pumps 210 or 230. In an example, the controller includes one or more computational circuitries for controlling pumps 210 or 230. As illustrated, the system 200 is a semi-batch system in which a first filtration system 202 undergoes a first cycle including an initiation with a population of hydrogel particles and a continuous draw of permeate along with an optional continuous feed a buffer solution. Following the cycle of the first filtration system, the permeate can be fed to initiate the second filtration system followed by continuous draw of a permeate and optional continuous feed of the buffer solution. After a cycle of the second filtration system 224, a retentate can be extracted that includes the desired subpopulation of hydrogel particles having a desired coefficient of variance, average particle size, and particle size distribution. Alternatively, the system can be set to operate in full batch mode or operate in continuous mode. While the system 200 includes filtering large particles prior to separating fine particles, alternatively, the filtration system can be reversed, separating fine particles prior to separating large particles In an example, the velocity across the first filter within the first filtration system 202 can be in a range of 0.01 cm/min to 0.17 cm/min. The velocity of the permeate is defined as the flowrate of the permeate divided by the cross-sectional area of the filter. For example, the velocity of the permeate can be in a range of 0.02 cm/min to 0.17 cm/min, such as a range of 0.05 cm/min to 0.16 cm/min, a range of 0.07 to 0.15 cm/min, or a range of 0.08 cm/min to 0.15 cm/min.

In a further example, the permeate velocity across the second filtration system 224 can be in a range of 0.01 cm/min to 0.17 cm/min. For example, the velocity of the permeate can be in a range of 0.02 cm/min to 0.14 cm/min, such as a range of 0.02 cm/min to 0.11 cm/min, a range of 0.02 cm/min to 0.085 cm/min, or a range of 0.02 cm/min to 0.075 cm/min.

In a particular example, the filtration system 202 has the same pore size as the filtration system 224. Extraction or separation from large particles relative to separation from fine particles can be accomplished by changing the velocity across the filtration system despite the equivalent pore sizes. Alternatively, the filtration systems can have different pore sizes. In a particular example, the pore size in both the filtration system 202 and the filtration system 224 can be larger than the desired average particle size of the resulting subpopulation. In particular, the pore sizes of the filtration systems 202 and 224 can be at least 10% greater than the desired particle size of the desired subpopulation of hydrogel particles. For example, the pore size of the filtration systems 202 and 224 can be at least 15% greater than the desired average particle size, such as at least 20% greater or even at least 25% greater than the desired average particle size. In a further example, the permeate velocity can be greater in filtration system 202 than the permeate velocity in the filtration system 224.

Depending on the desired target size range and the magnitudes of the flow rates of each filtration step, the filtrates or retentates from each filtration step can include particles having sizes in a desired range. For example, the average size of particles within the first retentate can typically be greater than the average particle size of the second retentate or the second filtrate, while the average size of particles within the second retentate can typically be greater than the average particle size of the second filtrate. In some embodiments, the first filtering step can be employed to remove particles having average sizes exceeding the desired target range by selectively retaining such particles within the first retentate. The second filtering step can be employed to selectively retain particles having average sizes within the desired range within the second retentate, while particles having average sizes smaller than the desired range can be carried away in the second filtrate. Optionally, the first filtering step, the second filtering step, or the first and second filtering steps can be repeated one or more times on any one or more of the resulting size-separated particle populations (e.g., the particle populations within the first retentate, the first filtrate, the second retentate or the second filtrate). In some embodiments, any one of the resulting size-separated particle populations (e.g., the particle populations within the first retentate, the first filtrate, the second retentate or the second filtrate) can be subjected to further washing, purification or concentration steps, or used in various biological applications of interest. For example, the particles of the second retentate can be washed and distributed onto surface to form a particle array. The particle array can then be subjected to a nucleic acid sequencing reaction, for example an ion-based sequencing reaction.

Typically, the CV of the first plurality of particles in the first retentate, or the second plurality of particles in the second retentate, or the third plurality of particles in the second filtrate is less than the CV of the polydisperse particle population prior to such purification. For example, in some embodiments, the polydisperse particle population prior to purification can have a CV of at least about 30%, 35%, 40%, or greater, and the CV of particles in the second retentate can be no greater than about 20%, 15%, 10% or 5%.

It is to be appreciated that for the reasons discussed above, maintaining the first and second flow rates during the two-step filtering through the filtration system allows for a second retentate with reduced CV even though the particles in the feed fluid may be flexible, deformable, or compressible. Without maintaining the first and second flow rates, such a result is difficult to achieve by simply filtering the feed fluid through two filters having different pore sizes due to the flexibility, deformability, or compressibility of the particles in the feed fluid. Furthermore, the technique of the present disclosure also allows for more convenience when the cut off sizes need to be varied. Conventionally, filters of different pore sizes would have to be acquired and switched out to allow for different cut off sizes. This may present a particularly difficult problem in tuning the CV when the filters of desired pore sizes are not readily available for sale. In comparison, it is much simpler to use the same or a similar filter and vary the flow rates to be maintained during the first and second steps of filtration.

Filtration may be applied to purify a sample including a population of polydispersed particles and decrease the coefficient of variation in the particle population. Some embodiments use one or more filters, across which a driving force is applied in order to induce components of a mixture to pass through the one or more filters. The portion of the sample that passes through the filter is referred to herein as the filtrate, whereas the portion that does not pass through the filter is referred to as the retentate. As the person of skill in the art can readily appreciate, particle retention by a filter can vary with various factors, including temperature, filter surface condition, e.g., degree of clogging or associated clearing rate, particle shape, structure, particle concentration, presence of other solutes and ionic conditions.

The driving force that drives a fluid across a filter medium is the pressure differential across the filter medium. In some embodiments, the pressure differential may be a positive pressure on the upstream side of the filter or a negative pressure on the downstream side of the filter. In some embodiments, a positive pressure on the upstream side may provide a force that pushes the retentate through the filter, and a negative pressure on the downstream side may provide a force that pulls the retentate through. A suitable pump on the upstream or downside side may be used to provide the positive or negative pressure, respectively. A positive pressure can also be provided by gravity or centrifugal force. A suitable pump may be any pump known in the art that is operable to satisfy the flow conditions discussed herein. An exemplary pump may be a syringe pump operable to maintain different flow rates through the filter. Depending on the design of the mechanism for providing the pressure different, different types of filters may be used. Some exemplary filters suitable for the technique of the present disclosure include pressure filter, vacuum filters, centrifugal filters, and gravity filters.

In some embodiments, the disclosure relates to methods, compositions and apparatuses using filters and involving adjustment of flow rate of a sample through the filter to control the degree to which particles of a given size within the sample can be retained under a given set of flow conditions, while other parameters are kept as constant as possible. In some embodiments, the disclosed methods exploit the fact that the effective size cutoff of a particular filter can be adjusted or "tuned" by varying the prevailing filtration conditions, particularly by varying the flow rate of the feed stream while other parameters are kept constant. For example, in some embodiments, the disclosed methods comprise filtering a sample through a filter at a first flow rate, where the filter has a first size cutoff at the first flow rate, and then changing the size cutoff of the filter by changing the flow rate of the sample. Typically, the size cutoff of the filter can be increased by increasing the flow rate of the sample feed, and can be decreased by decreasing the flow rate of the sample feed.

In some embodiments, the disclosure relates generally to methods of purifying a sample including a population of polydisperse particles using filtration, thereby decreasing the coefficient of variation in the particle population. Such methods typically use one or more filters, across which a driving force is applied in order to induce components of a reaction mixture to pass through the one or more filters. The portion of the sample that passes through the filter is referred to herein as the filtrate or permeate, whereas the portion that does not pass through the filter is referred to as the retentate. Particle retention by a filter can vary due to particle shape, structure, particle concentration, presence of other solutes and ionic conditions. The disclosure focuses on the adjustment of flow rate as a means for controlling the degree to which particles of a given size can be retained under a given set of flow conditions, while other parameters are kept approximately constant.

In some embodiments, the disclosure relates generally to use of one or more filters having a first size cutoff value when filtering a feed at a first flow rate, and having a second size cutoff value when filtering a feed at a second flow rate but under otherwise substantially identical conditions. For example, a filter can be used to filter a sample feed at a first flow rate, where the filter has a first size cutoff at the first flow rate, and then used to filter a sample feed at a second flow rate, where the filter has a second size cutoff at the second flow rate. In some embodiments, the disclosed methods (and related compositions, systems, apparatuses and kits) comprise filtering a sample including a population of particles of varying sizes through a filter at a first flow rate, thereby retaining a plurality of particles having a size greater than a first cutoff value and producing a first filtered sample; and filtering the first filtered sample through the filter at a second flow rate, thereby retaining a plurality of particles having a size greater than a second cutoff value and producing a second filtered sample. In some embodiments, the first flow rate is greater than the second flow rate, and the first cutoff value is greater than the second cutoff value. Alternatively, the first flow rate can be less than the second flow rate, and the first cutoff value can be less than the second cutoff value.

In some embodiments, the disclosure relates generally to filtering a sample through a filter at a first flow rate, thereby producing a first filtered sample, and filtering the first filtered sample through the filter at a second flow rate, thereby producing a second filtered sample, where the filter has a first size cutoff at the first flow rate and a second size cutoff at the second flow rate.

In some embodiments, the sample is applied to a filter at a first flow rate under conditions where the filter has a first size cutoff, thereby producing a first filtered sample. The first filtered sample is then applied to the same filter (or to a second filter that is substantially identical to the first) at a second flow rate under conditions where the filter (or second filter) has a second size cutoff.

In some embodiments, the disclosure relates generally to controlling the size cutoff of a filter by adjusting the flow rate at which a sample feed is applied to the filter, comprising: applying a sample feed to a first filter using a first set of flow conditions, thereby producing a first filtered sample; and applying the first filtered sample to a second filter at a second set of flow rate conditions, where the first and second filters have a first size cutoff at the first set of flow rate conditions and the first and second filters have a second size cutoff at the second set of flow rate conditions. In some embodiments, the first and second filters have the same composition and dimensions.

In some embodiments, the sample feed including the particle population is filtered successively through two substantially identical filters; however, the sample is applied to each of the two substantially identical filters at different flow rates, and the effective size cutoff of each filter varies with the flow rate of the sample feed. For example, in some embodiments the disclosure relates generally to using two separate filters (referred to as the first and second filters respectively) to successively filter the same sample feed, where the sample feed is applied to the first filter at a first flow rate, thereby producing a first filtered sample; and the first filtered sample is applied to the second filter at a second flow rate, thereby producing a second filtered sample, where the first filter has a first size cutoff at the first flow rate and the second filter has a second size cutoff at the second flow rate. In some embodiments, the first flow rate is greater than the second flow rate, and the first cutoff value is greater than the second cutoff value. Alternatively, the first flow rate can be lesser than the second flow rate, and the first cutoff value can be lesser than the second cutoff value. The two filters can be of the same type, e.g., have substantially identical compositions and exhibit substantially the same pore size under a given set of conditions and exhibit substantially the same size cutoff at a given sample flow rate. For example, the filters can be two substantially identical samples of the same product provided by a manufacturer under the same catalog or product number.

In some embodiments, the disclosure relates generally to purifying a sample feed including a population of polydisperse particles by filtering the sample feed stream at a first flow rate through a first filter, thereby producing a first filtered sample; and filtering the first filtered sample at a second flow rate through a second filter, where the first filter has a first size cutoff at the first flow rate and the second filter has a second size cutoff at the second flow rate. Optionally, the second filter also has the first size cutoff at the first flow rate, and the first filter also has the second size cutoff at the second flow rate. Optionally, the filtering the sample feed stream through the first filter includes retaining a plurality of particles having a size greater than the first size cutoff, and filtering the first filtered sample through the second filter includes retaining a plurality of particles having a size greater than the second size cutoff.

In some embodiments, the disclosed methods, compositions, systems, apparatuses and kits relate generally to purifying a sample population of polydisperse particles, comprising applying the sample at a first flow rate to a first filter having a first effective particle size cutoff; filtering the sample through the first filter, thereby producing a first filtration filtrate and a first filtration retentate; and filtering the first filtration filtrate through a second filter at a second flow rate, where second filter has a second effective particle size cutoff at the second flow rate, and where the first and second filter have substantially identical compositions or dimensions.

The size cutoff refers to the ability of a given filtration membrane (or filtration resin) to retain a given percentage (typically 90%) of a solute of a defined size (typically measured as length along any one dimension). In the case of particle populations comprising roughly spherical or spheroidal particles, the size of a particle is typically measured as the average diameter of the particle in metric length units (e.g., millimeters, nanometers or micrometers). In some embodiments, the size cutoff can be measured in terms of the average molecular weight of the particle in kiloDaltons (kD).

The flow rate of the sample typically refers to the rate of flow of filtrate across the filtration member (or through the filtration resin), and is typically measured as the total amount of filtrate fluid crossing the membrane per unit time, recorded as liters per minute (L/min) or milliliters per minute (mL/min). In some embodiments, the flow rate of filtrate across the membrane can also be divided by the total area of the membrane (or cross-sectional area of the resin) to produce a flux rate measured in Liters/minute/ft2 or Liters/minute/m2. In some embodiments, the flow rate can be approximated by measuring the volume of fluid withdrawn by the syringe per unit time in a filtration system fed by a syringe pump. The flow rate can be measured at the retentate rather than the filtrate (for example in a tangential flow filtration system) and recorded as liters per minute (L/min) or milliliters per minute (mL/min). The velocity can be expressed as the flowrate across a membrane or filter divided by the area of the membrane or filter and is recorded as cm/min.

Any suitable form or filter configuration can be employed when practicing the disclosed methods, compositions, systems, apparatuses and kits. In particular, the filter can be a track-etched membranes with a relatively uniform pore size distribution. In some embodiments, a direct flow filtration process can be used, wherein the feed is directed into the filter membrane (or resin). Alternatively a tangential flow filtration process can be employed, wherein the sample solution flows through the feed channel and along, e.g., tangential to, the surface of the membrane or resin, as well as through the membrane or resin. The resulting crossflow can help to prevent build up of molecules at the surface that can cause fouling.

The disclosed methods (and related compositions, systems, apparatuses and kits) can be useful in purifying particle populations so as to increase the monodispersity of the population. While particle populations are useful in a variety of applications, the methods used to synthesize such populations can result in size variability of the resulting population. Typically, such size variability is undesirable and can decrease the utility of the population in various applications. One measure of the size variability within a particle population is the coefficient of variation (CV). The coefficient of variation (CV) is typically measured as 100 times (standard deviation) divided by average where "average" is mean particle diameter and standard deviation is standard deviation in particle size. The disclosure also includes embodiments where the "average" is either the z-average or mode particle diameter. In some embodiments, and in accordance with known practice, CV can be calculated on the main mode, i.e., the main peak, thereby excluding minor peaks relating to aggregates. Thus some particles below or above mode size may be discounted in the CV calculation which may for example be based on about 90% of total particle number (i.e., total number of detectable particles). Typically, the CV of a particle population is determined via fluorescence microscopy as described in Example 1, or using CPS disc centrifugation or any other suitable method for measuring the CV of a particle population.

A monodisperse particle population typically has a low coefficient of variation (CV) of a specific parameter (e.g. particle diameter), for example a CV of less than 20% and is particular of less than 15%, e.g. of less than 10% and sometimes of less than 5%. For example, a monodisperse particle population typically includes a plurality of particles (e.g. at least 100, more preferably at least 1000) having a coefficient of variation (CV) of their diameters of less than about 20%, for example less than about 15%, optionally less than 10%, less than about 8%, or less than about than 5%. In some embodiments, the particle population has a CV of less than about 5%.

In some embodiments, the disclosure relates generally to methods of purifying a sample including a population of polydisperse particles (referred to as the "polydisperse particle population") so as to reduce the CV of the polydisperse particle population. Typically, such purifying includes removing from the polydisperse particle population a first plurality of particles having an average size greater than a first cutoff value, and removing a second plurality of particles having an average size less than a second cutoff value. Removing the first plurality of particles can include filtering the sample through a first filter at a first flow rate, where the first filter has a first size cutoff at the first flow rate, thereby producing a first retentate including the first plurality of particles, and a first filtrate. Removing the second plurality of particles can include filtering the first filtrate through a second filter at a second flow rate, thereby producing a second filtrate that includes the second plurality of particles, and a second retentate including a purified particle population. Typically, the CV of the purified particle population is less than the CV of the polydisperse particle population.

In some embodiments, the disclosure relates generally to methods (and related compositions, systems and apparatuses) for purifying a polydisperse particle population of scaffolded nucleic acid polymer particles having a CV of at least 35% using two substantially identical filters including a first filter and a second filter, where the polydisperse particle population is first filtered through the first filter at a first flow rate, the first filter having a first size cutoff at the first flow rate, thereby producing a first retentate including a first plurality of particles having an average size that is greater than the first size cutoff, and a first permeate. The first permeate is optionally filtered through the second filter at a second flow rate, the second filter having a second size cutoff at the second flow rate, thereby producing a second retentate including a second plurality of particles having an average size that is greater than the second size cutoff, and a second permeate including a third plurality of particles having an average size that is lesser than the second size cutoff. Alternatively, the filters can have different pore size and operate at different flow rates or velocities.

Depending on the desired target size range and the magnitudes of the flow rates of each filtration step, the permeates or retentates from each filtration step can include particles having sizes in a desired range. For example, the average size of particles within the first retentate can typically be greater than the average particle size of the second retentate or the second permeate, while the average size of particles within the second retentate can typically be greater than the average particle size of the second permeate. In some embodiments, the first filtering step can be employed to remove particles having average sizes exceeding the desired target range by selectively retaining such particles within the first retentate. The second filtering step can be employed to selectively retain particles having average sizes within the desired range within the second retentate, while particles having average sizes smaller than the desired range can be carried away in the second permeate. Optionally, the first filtering step, the second filtering step, or the first and second filtering steps can be repeated one or more times on any one or more of the resulting size-separated particle populations (e.g., the particle populations within the first retentate, the first permeate, the second retentate or the second permeate). In some embodiments, any one of the resulting size-separated particle populations (e.g., the particle populations within the first retentate, the first permeate, the second retentate or the second permeate) can be subjected to further washing, purification or concentration steps, or used in various biological applications of interest. For example, the particles of the second retentate can be washed and distributed onto surface to form a particle array. The particle array can then be subjected to a nucleic acid sequencing reaction, for example an ion-based sequencing reaction.

Typically, the CV of the first plurality of particles in the first retentate, or the second plurality of particles in the second retentate, or the third plurality of particles in the second permeate is less than the CV of the polydisperse particle population prior to such purification. For example, in some embodiments, the polydisperse particle population prior to purification can have a CV of at least about 30%, 35%, 40%, or greater, and the CV of particles in the second retentate can be no greater than about 20%, 15%, 10%, or 5%.

In some embodiments, the individual particles in a fluid, such hydrogel matrices, may be flexible, deformable, or compressible, making the filtration of these particles by size selection difficult. For example, in some exemplary embodiments, the particles of the polydisperse particle population include semi-solid particles comprising aqueous hydrogel matrices, such as those disclosed, for example, in U.S. Pub. No. 2010/0136544 published Jun. 3, 2010; as well as in U.S. Ser. No. 12/785,685, filed May 24, 2010 and titled "Scaffolded Nucleic Acid Polymer Particles and Methods of Making and Using", now published as U.S. Pub. No. 2010/0304982 on Dec. 2, 2010; U.S. Ser. Nos. 12/474,897, now published as U.S. Pub. No. 2010/0137143 on Jun. 3, 2010 and 12/475,311, filed 29 May 2009 and published as U.S. Pub. No. 2010/0301398 on Dec. 2, 2010; U.S. Ser. No. 61/263,734 filed 23 Nov. 2009; U.S. Ser. No. 61/291,788 filed 31 Dec. 2009; U.S. Ser. No. 61/297,203 filed 21 Jan. 2010; and International Application No. PCT/US2010/001549, filed May 27, 2010 and published as WO 2010/138187 on Dec. 2, 2010, all of which are incorporated herein by reference in their entireties. As described therein, such particles can be useful as supports for nucleic acid templates, typically distributed clonally over various particles, such that each particle includes a clonal population of nucleic acid molecules. Such clonal nucleic acid containing particles can be distributed across a surface to form a nucleic acid array, which can then be subjected to various treatments such as ion-based sequencing reactions. See, e.g., U.S. Pub. Nos. 2010/0304982, 2010/0137143 and 2010/0301398.

The flexibility, deformability, or compressibility of the hydrogel matrices may allow them to pass through pores that are smaller than the size of the hydrogel matrices if sufficient compressive force is present on the upstream side. The size of hydrogel matrices that can pass through the smaller pores of the filter can increase as the compressive force on the upstream side increases. As such, a large variation in the size of hydrogel matrices in the retentate may be resulted when the design of filtration system introduces variable flow condition on the upstream side. For example, a positive pressure applied may develop a gradient near the upstream side of the filter membrane, thereby introducing variable compression of the hydrogel matrices. Accumulation of particles at the upstream side of the filter membrane is another source of variable compression. As such, the disclosed embodiments in present disclosure that minimizes variation in the upstream side may have particular synergistic advantage when used to filter fluids containing hydrogel matrices or other particles that are flexible or compressible. In particular, maintaining a constant flow rate as opposed to a constant pressure differential is one effective way to minimize variation in the upstream side, and has particular synergistic application for filtering flexible, deformable, or compressible particles. In an exemplary embodiment, a negative pressure is applied on the downstream side of the filter to draw a fluid through the filter. The negative pressure on the downstream side creates little or no gradient on the upstream side of filter, thereby minimizing the variable compression on the upstream side. Furthermore, in an exemplary embodiment, the filter may include a stirrer operable to minimize accumulation of particles at the upstream side of the filter membrane, thereby reducing clogging and further alleviating the problem of variable compression.

EXAMPLES

The following non-limiting examples are provided purely by way of illustration of exemplary embodiments, and in no way limit the scope and spirit of the present disclosure. Furthermore, it is to be understood that any inventions disclosed or claimed herein encompass all variations, combinations, and permutations of any one or more features described herein. Any one or more features may be explicitly excluded from the claims even if the specific exclusion is not set forth explicitly herein. It should also be understood that disclosure of a reagent for use in a method is intended to be synonymous with (and provide support for) that method involving the use of that reagent, according either to the specific methods disclosed herein, or other methods known in the art unless one of ordinary skill in the art would understand otherwise. In addition, where the specification or claims disclose a method, any one or more of the reagents disclosed herein may be used in the method, unless one of ordinary skill in the art would understand otherwise.

Example 1

Using the Same Filter to First Remove Large Aggregates and then Remove Fines from a Sample Population of Scaffolded Nucleic Acid Polymer Particles A polydisperse particle population of scaffolded nucleic acid polymer particles having a CV of between about 40% and 50% is purified by subjecting the polydisperse particle population to two successive filtrations, using two identical filters but different flow rates for each filtration. The objective is to obtain a relatively monodisperse particle population (CV no greater than about 20%) having an average particle diameter of about 1.5 microns. Both filtration steps employ a Millipore polycarbonate filter having an average pore size of about 2 microns and a membrane diameter of about 47 mm (Millipore catalog #TTTP04700). The first filtration is performed at a higher flow rate (1.5 mL/min) to remove "large" aggregates having an average size (diameter) significantly greater than 1.5 microns, while the second filtration is performed at a lower flow rate (10 mL/min) to remove "fines" having an average size (diameter) significantly lower than about 1.5 microns. This two-step purification yields a purified population of nucleic acid polymer particles having an average diameter of 1.5 microns having a CV of about 13% with few outliers. The CV is estimated using fluorescence microscopy. Briefly, fluorescently stained nucleic acid polymer particles are first immobilized on a microscope slide via centrifugation, and microscope images of the immobilized particles are obtained at 1000× magnification. Software analysis of the images is performed to measure the diameter of the immobilized particles in the images, normally using a sample size of 1000 to 3000 particles.

The purification protocol is as follows. Briefly, the initial polydisperse particle population including nucleic acid polymer particles from bulk synthesis reactions is first filtered using a direct flow filtration system including a 2 micrometer pore size membrane (Millipore catalog #TTTP04700). A schematic of the filtration apparatuses (See FIG. 1) is provided, and includes a stir cell attached to a syringe vacuum pump and a membrane filter (Millipore catalog #TTTP04700). The stir cell and associated tubing is first cleaned; the filter is inserted and the bulk nucleic acid polymer particle sample is diluted to a total volume of 285 mL buffer. The membrane is first primed by pulling 8 mL buffer through the filter at a rate of 1.5 mL/minute using the syringe pump. The diluted bulk nucleic acid polymer population is added to the stir cell, which is then sealed; 900 mL of solution are then filtered through the filter with syringe pump drawing filtrate at a flow rate of 1.5 mL/min for a period of approximately 16 hours. During the filtration, the fluid volume is diluted with SNAPP buffer solution to maintain the fluid volume in the stir cell.

The permeate from the first filtration step ("first permeate") is collected and then concentrated to 100 mL volume using tangential flow. Meanwhile, the filter apparatus including the stir cell is disassembled, washed and equipped with a fresh filter membrane (Millipore catalog #TTTP04700). This membrane is the same type (Millipore catalog #TTTP04700) and had the same composition and pore size as the membrane used in the first filtration.

The concentrated first permeate is then diluted to a volume of 268 mL and subjected to a second filtration yielding a second retentate and second permeate. The fresh filter is primed by pulling 8 mL of buffer at a rate of 1.5 mL/minute using the syringe pump. The diluted bulk first permeate is added to the stir cell, which is then sealed; 200 mL of solution are then filtered through the second filter with syringe pump drawing filtrate at a flow rate of 1 mL/min to produce a second retentate that is re-diluted to 260 mL after each 200 mL cycle. This lower speed causes a change in the effective cutoff for the filtration membrane. The second filtration is repeated for a total of 5 times; each round of filtration is performed for approximately 4 hours each.

As shown in the attached figures, the purity (in terms of reduction in observed size distribution) increases, and the CV of the particle population in the filtrate correspondingly decreases, with each successive round of filtration, as indicated in the attached figures.

Figure 3A:
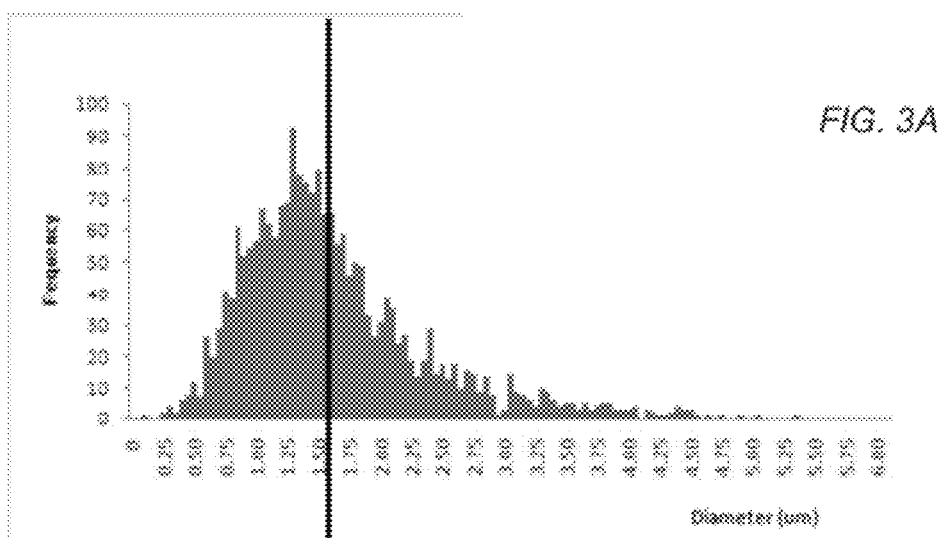
FIG. 3A, FIG. 3B, FIG. 3C, FIG. 4A, FIG. 4B, FIG. 5A and FIG. 5B include graphical illustrations of exemplary hydrogel particle size distributions.
Figure 3B:
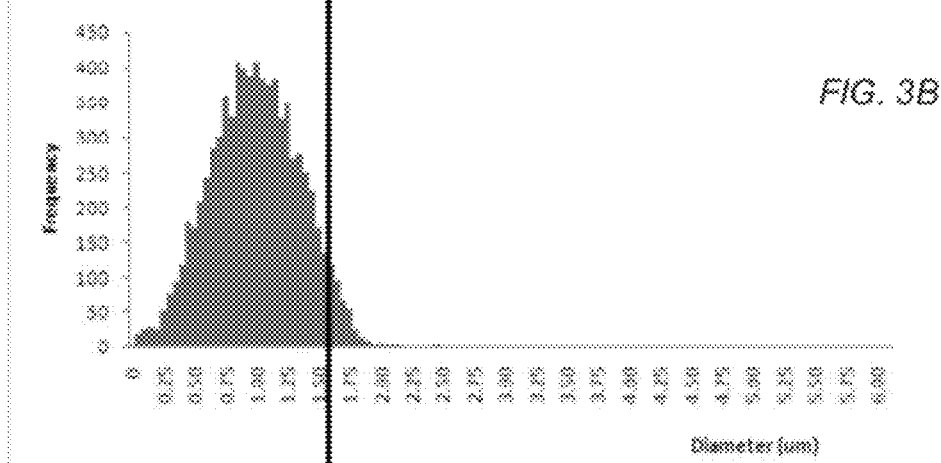
Figure 3C:
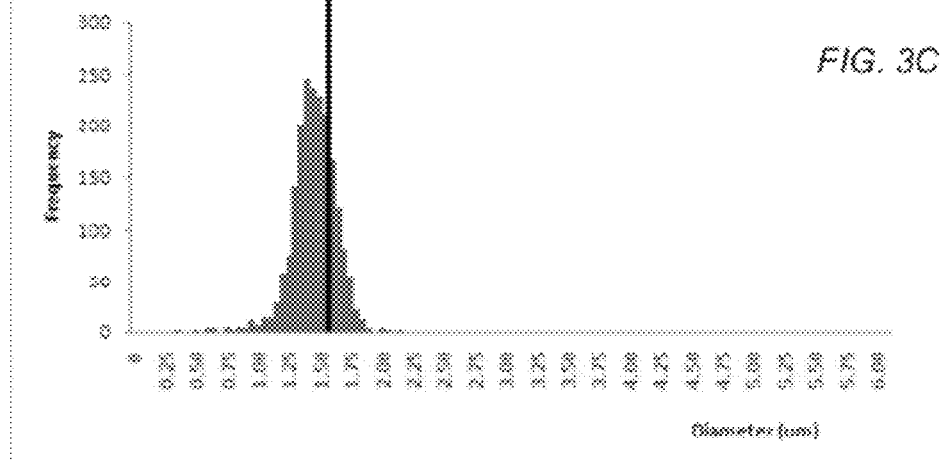

For example, FIG. 3A illustrates an initial particle size distribution prior to filtration. FIG. 3B illustrates the particle size distribution after removal of the larger particles. Despite the filter being a 2 micrometer filter, a portion of the particles having size less than 2 micrometers are separated and remain in the retentate, while the remaining subpopulation having particle size less than 2 micrometer follows the permeate. FIG. 3C illustrates the particle size distribution following the separation of the fine particles. Despite using a 2 micrometer filter, particles in a range of 1.25 micrometers to 1.7 micrometers remain in the retentate and particles having a particle size less than 1.25 micrometers pass through with the permeate. The lower flowrate appears to select for smaller particle size passing through the filter into the permeate.

Figure 4A:
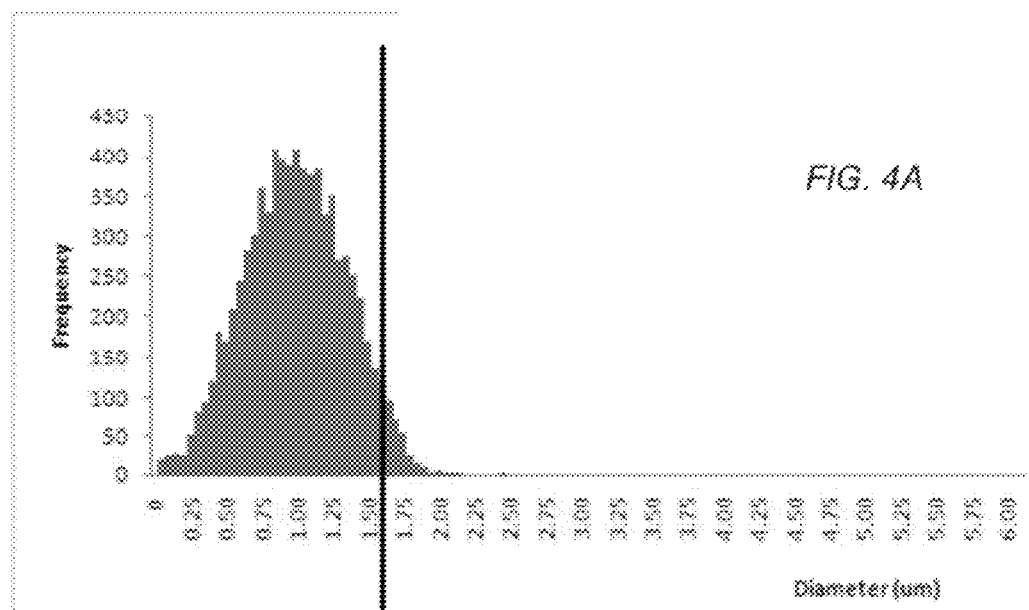
Figure 4B:
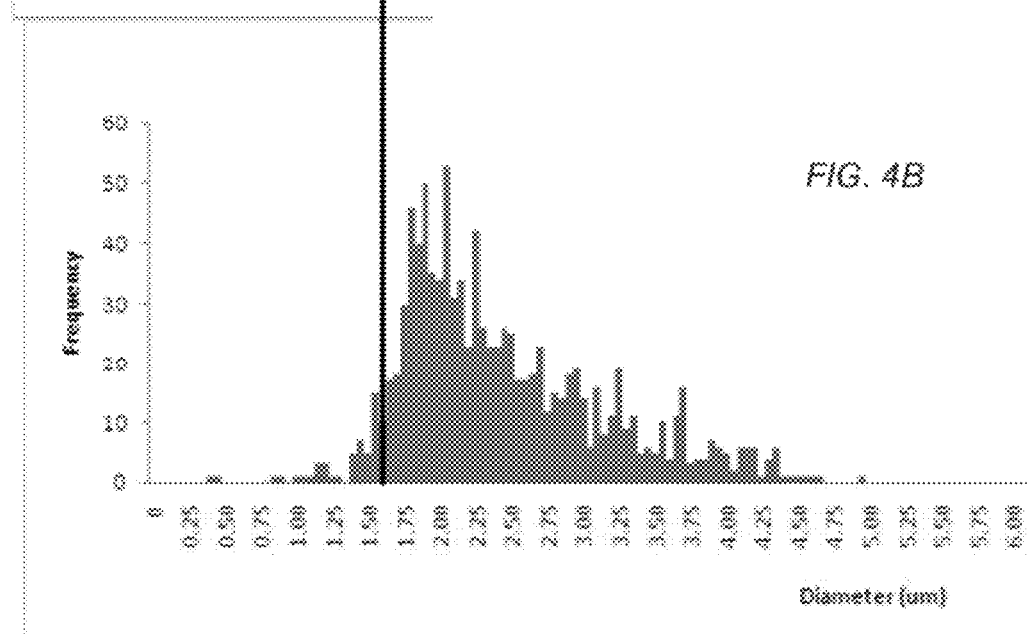

The selection phenomenon is further illustrated in FIG. 4A and FIG. 4B. FIG. 4A illustrates the population of hydrogel particles within the permeate and FIG. 4B illustrates particles within the retentate following large particle separation. Recognizing that the filter pore size is approximately 2 micrometers, at the selected flowrate, particles having a size greater than 1.5 micrometers can be retained in the retentate while at least some particles smaller than approximately 1.75 micrometers following the permeate.

Figures 5A, 5B:
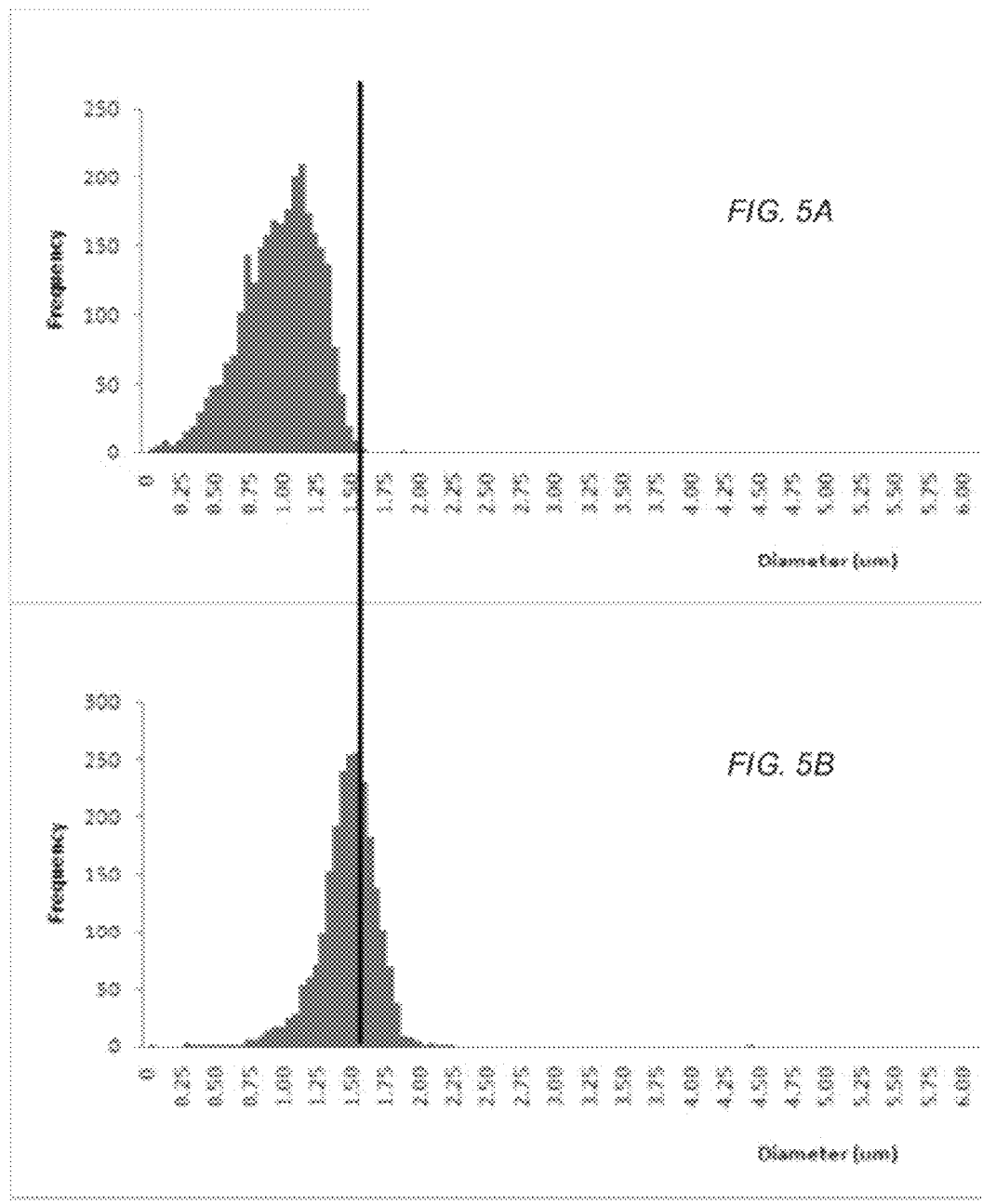
Figure 6:
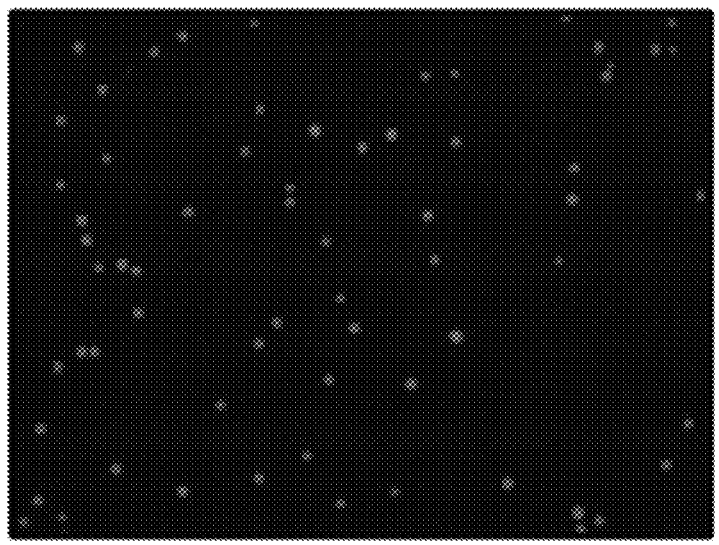
FIG. 6 includes a pictorial image of exemplary filtered hydrogel particles.

As further illustrated in FIG. 5A and FIG. 5B, permeate flow can affect the separation of smaller particle sizes. FIG. 5A illustrates the particle size distribution for the permeate and FIG. 5B illustrates the particle size distribution of the retentate. Given a 2 micrometer filter pore size at low flowrate, fine particles having particle size less than 1.25 micrometers are preferentially withdrawn in the permeate, while particles in a range of 1.25 micrometers to 1.75 micrometers are selectively retained within the retentate. The resulting retentate particle distribution has an average particle size of less than the pore size of the filter, yet is narrow and has a low coefficient of variance. FIG. 6 illustrates the resulting subpopulation of hydrogel particles, which exhibit relatively uniform particle size.

Figure 7:
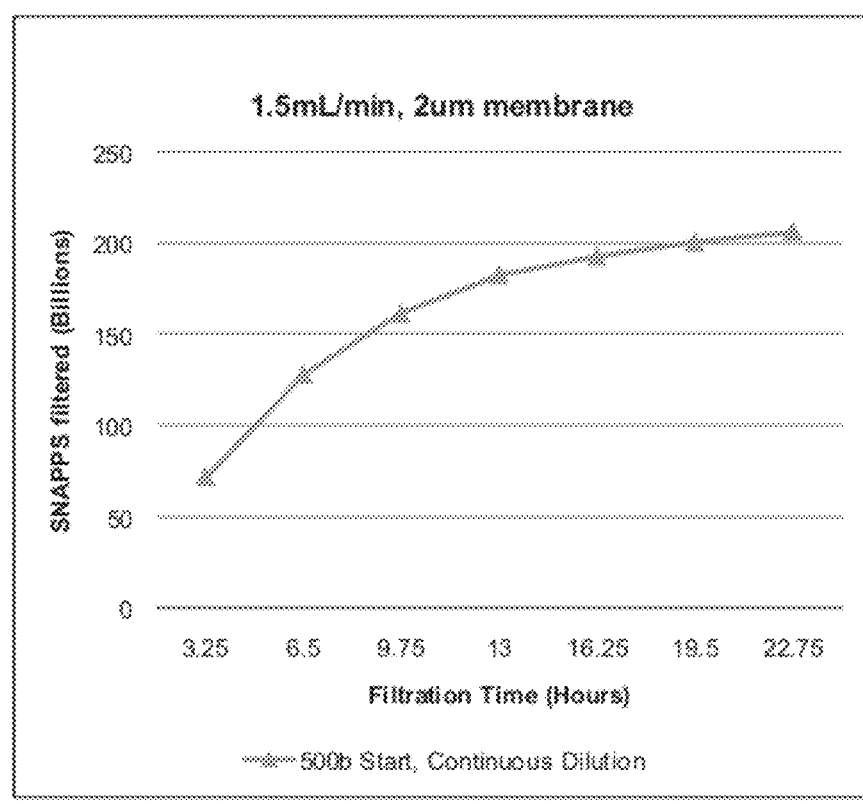
FIG. 7 and FIG. 8 include graphical illustrations of filtration performance.
Figure 8:
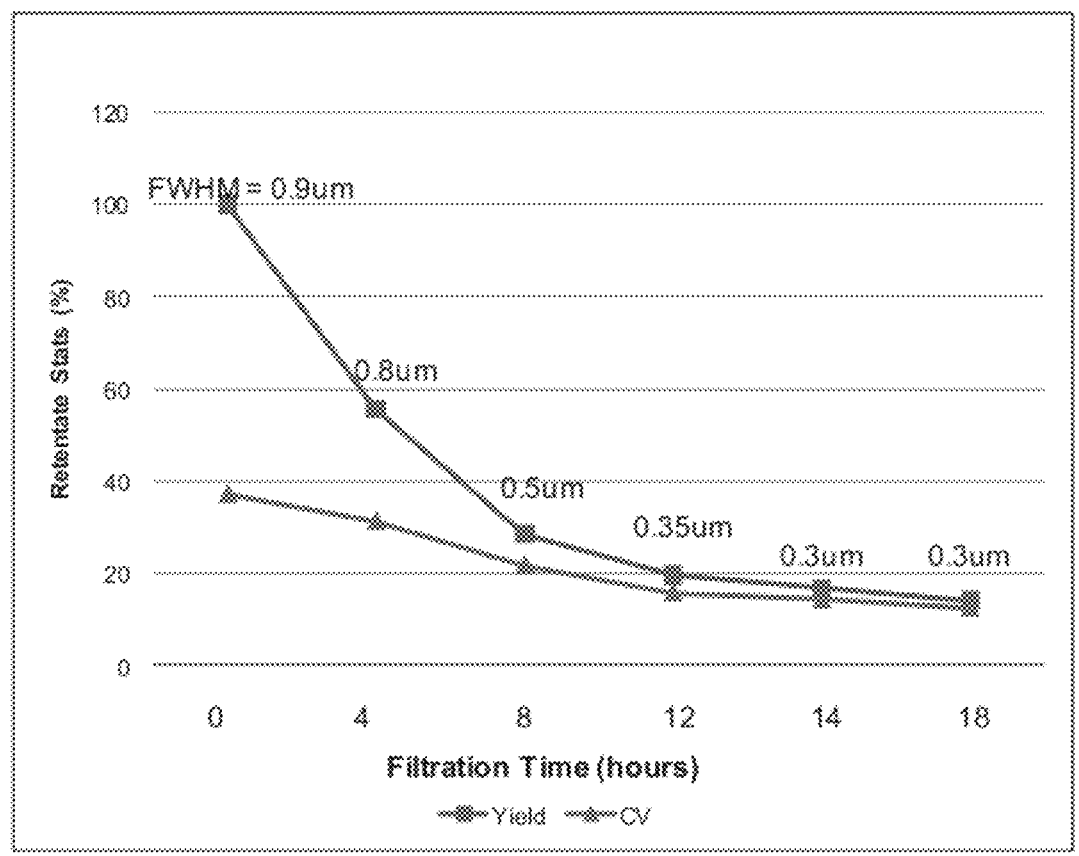
Figure 9:
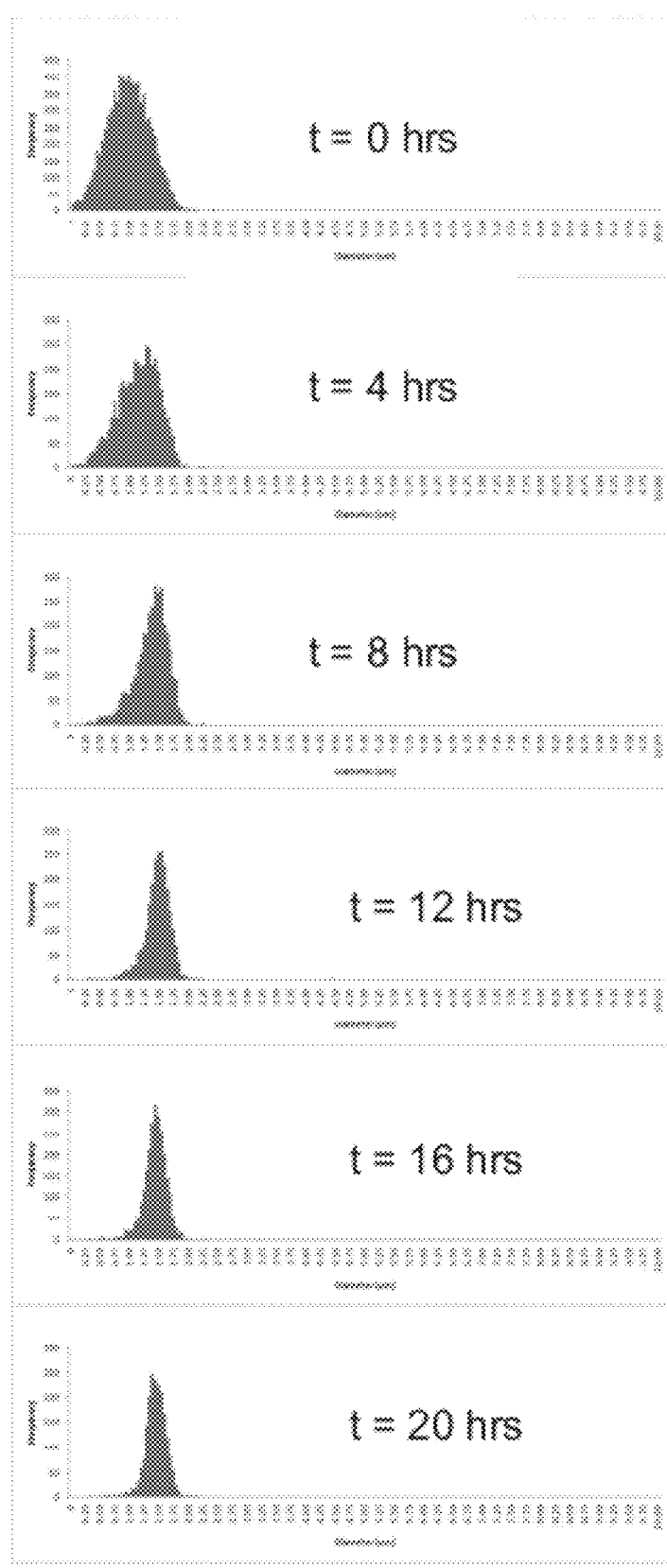
FIG. 9 is a graphical illustration of the particle distributions as a distribution changes over time.

It is further demonstrated that selectivity for particle size is retained even during long filtration cycles. As illustrated in FIG. 7, the number of particles filtered approaches an asymptote following long filtration cycles. As such, the larger particles tend to remain within the retentate even through long filtration cycles. Further, as illustrated in the graph of FIG. 8, the yield and coefficient of variance both approach an asymptote over long filtration cycles when separating finer particles. In particular, the particle size distribution narrows around an average particle size as demonstrated by the reduction in Full Width at Half Maximum (FWHM), annotated on the graph of FIG. 8. Over the 18 hours of the filtration cycle, the FWHM is reduced from 0.9 micrometers to 0.3 micrometers for a population having an average particle size of approximately 1.5 micrometers. Such narrowing is further illustrated in FIG. 9, which includes graphical illustrations of the population distribution as a function of filtration cycle time. Through the cycle, the distribution is shown to be narrowing. In addition, the average particle size increases as fine particles are removed.

As such, it is demonstrated that despite a filter having a pore size greater than the desired average particle size, the particle size distribution can be manipulated by changing the permeate velocity across the filter.

In a first aspect, a method of preparing polymeric particles includes filtering a plurality of polymeric particles through a first filter having a pore size at a first permeate velocity to provide a first subset of polymeric particles; and filtering the first subset of polymeric particles through a second filter having the pore size at a second permeate velocity to provide a second subset of polymeric particles; wherein the first and second permeate velocities are different.

In an example of the first aspect the first subset of hydrogel particles are of a permeate product and the second subset of polymeric particles are of a retentate product.

In another example of the first aspect and the above example, the first permeate velocity is greater than the second permeate velocity.

In a further example of the first aspect and the above examples, the first permeate velocity is in a range of 0.01 cm/min to 0.17 cm/min, a range of 0.02 cm/min to 0.17 cm/min, a range of 0.05 cm/min to 0.16 cm/min, a range of 0.07 to 0.15 cm/min, or a range of 0.08 cm/min to 0.15 cm/min.

In an additional example of the first aspect and the above examples, the second permeate velocity is in a range of 0.01 cm/min to 0.17 cm/min, a range of 0.02 cm/min to 0.14 cm/min, a range of 0.02 cm/min to 0.11 cm/min, a range of 0.02 cm/min to 0.085 cm/min, or a range of 0.02 cm/min to 0.075 cm/min.

In another example of the first aspect and the above example the polymeric particles are hydrogel particles.

In a second aspect, a method of preparing polymeric particles includes filtering a plurality of polymeric particles through a first filter having a first pore size at a first permeate velocity to provide a first subset of polymeric particles having a first average particle size; and filtering the first subset of polymeric particles through a second filter having a second pore size at a second permeate velocity to provide a second subset of polymeric particles having a second average particle size greater than the first average particle size; wherein the first and second pore sizes are at least the second average particle size.

In an example of the second aspect, the first pore size is greater than the second pore size.

In another example of the second aspect and the above examples, the first and second pore sizes are approximately equal. For example, the first permeate velocity is greater than the second permeate velocity.

In a further example of the second aspect and the above examples, the first permeate velocity is in a range of 0.01 cm/min to 0.17 cm/min, a range of 0.02 cm/min to 0.17 cm/min, a range of 0.05 cm/min to 0.16 cm/min, a range of 0.07 to 0.15 cm/min, or a range of 0.08 cm/min to 0.15 cm/min.

In an additional example of the second aspect and the above examples the second permeate velocity is in a range of 0.01 cm/min to 0.17 cm/min, a range of 0.02 cm/min to 0.14 cm/min, a range of 0.02 cm/min to 0.11 cm/min, a range of 0.02 cm/min to 0.085 cm/min, or a range of 0.02 cm/min to 0.075 cm/min.

In another example of the second aspect and the above examples the polymeric particles are hydrogel particles.

In a third aspect, a method of preparing hydrogel particles includes applying a solution including a plurality of hydrogel particles to a stir cell, a retentate side of a filter defining a lower surface of the stir cell, the filter having the retentate side and a permeate side; and while stirring the solution within the stir cell, drawing a permeate from the permeate side of the filter using a pump at a first flow rate, the permeate including a subset of the plurality of hydrogel particles.

In an example of the third aspect, the pump is a syringe pump.

In another example of the third aspect and the above examples, dispensing a buffer solution at a second flow rate to the stir cell. For example, the first and second flow rate are approximately equal.

In a further example of the third aspect and the above examples the velocity of the permeate across the filter is in a range of 0.01 cm/min to 0.17 cm/min, a range of 0.02 cm/min to 0.17 cm/min, a range of 0.05 cm/min to 0.16 cm/min, a range of 0.07 to 0.15 cm/min, or a range of 0.08 cm/min to 0.15 cm/min.

In an additional example of the third aspect and the above examples the method further includes applying the permeate to a second stir cell, a retentate side of a second filter defining a lower surface of the second stir cell, the second filter having the retentate side and a permeate side; and while stirring within the second stir cell, drawing from the permeate side of the second filter using a second pump at a third flow rate; and collecting a second subset of hydrogel particles from the retentate side of the second filter after a period of time.

In another example of the third aspect and the above examples a velocity across the second filter is in a range of 0.01 cm/min to 0.17 cm/min, a range of 0.02 cm/min to 0.14 cm/min, a range of 0.02 cm/min to 0.11 cm/min, a range of 0.02 cm/min to 0.085 cm/min, or a range of 0.02 cm/min to 0.075 cm/min.

In a further example of the third aspect and the above examples the second pump is a syringe pump.

In an additional example of the third aspect and the above examples, the filter has a larger pore size than the second filter.

In another example of the third aspect and the above examples the filter and the second filter have approximately the same pore size.

In a further example of the third aspect and the above examples the velocity across the filter is greater than the velocity across the second filter.

In an additional example of the third aspect and the above examples the average particle size of the second subset of hydrogel particles is in a range of 0.3 micrometers to 1.5 micrometers.

In another example of the third aspect and the above examples wherein the coefficient of variance of the second subset of hydrogel particles is not greater than 5.0%.

In a fourth aspect, a method of preparing hydrogel particles includes applying a solution including a plurality of hydrogel particles to a first stir cell, a retentate side of a first filter defining a lower surface of the first stir cell, the first filter having the retentate side and a permeate side, the first filter having a first pore size; and while stirring the solution within the first stir cell, dispensing a first buffer solution at a first flow rate to the first stir cell; and drawing a permeate from the permeate side of the first filter using a first pump at a second flow rate, the permeate including a subset of the plurality of hydrogel particles; applying the permeate to a second stir cell, a retentate side of a second filter defining a lower surface of the second stir cell, the second filter having the retentate side and a permeate side, the second filter having a second pore size; and while stirring within the second stir cell, dispensing a second buffer solution at a third flow rate to the second stir cell; and drawing from the permeate side of the second filter using a second pump at a fourth flow rate; and collecting a second subset of hydrogel particles from the retentate side of the second filter after a period of time; wherein the first and second pore size are the same.

In an example of the fourth aspect, the first and second buffer solutions have the same composition.

In another example of the fourth aspect, the average particle size of the second subset of hydrogel particles is in a range of 0.3 micrometers to 1.5 micrometers.

In an additional example of the fourth aspect and the above examples, the coefficient of variance of the second subset of hydrogel particles is not greater than 5.0%.

In a fifth aspect, a plurality of particles wherein a subset of the plurality of particles comprise hydrogel and the plurality of particles has a coefficient of variance of not greater than 5%, In an example of the fifth aspect, the particles are formed by the method comprising: applying a solution including a plurality of hydrogel particles to a first stir cell, a retentate side of a first filter defining a lower surface of the first stir cell, the first filter having the retentate side and a permeate side, the first filter having a first pore size; and while stirring the solution within the first stir cell, dispensing a first buffer solution at a first flow rate to the first stir cell; and drawing a permeate from the permeate side of the first filter using a first pump at a second flow rate, the permeate including a subset of the plurality of hydrogel particles; applying the permeate to a second stir cell, a retentate side of a second filter defining a lower surface of the second stir cell, the second filter having the retentate side and a permeate side, the second filter having a second pore size; and while stirring within the second stir cell, dispensing a second buffer solution at a third flow rate to the second stir cell; and drawing from the permeate side of the second filter using a second pump at a fourth flow rate; and collecting a second subset of hydrogel particles from the retentate side of the second filter after a period of time.

In a sixth aspect, a system includes a buffer container to store a buffer solution; a first stir cell including a first filter defining a lower surface of the first stir cell, the first filter having a first pore size, the buffer container in fluid communication with the first stir cell; and a first pump in fluid communication with a permeate side of the first filter; a second stir cell including a second filter defining a lower surface of the second stir cell, the second filter having a second pore size less than the first pore size; and a second pump in fluid communication with a permeate side of the second filter.

In an example of the sixth aspect the system further include a second buffer container in fluid communication with the second stir cell.

Note that not all of the activities described above in the general description or the examples are required, that a portion of a specific activity may not be required, and that one or more further activities may be performed in addition to those described. Still further, the orders in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

As used herein, the terms "comprises," "comprising," "includes," "including," "has," "having" or any other variation thereof, are intended to cover a non-exclusive inclusion. For example, a process, method, article, or apparatus that comprises a list of features is not necessarily limited only to those features but may include other features not expressly listed or inherent to such process, method, article, or apparatus. Further, unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

Also, the use of "a" or "an" are employed to describe elements and components described herein. This is done merely for convenience and to give a general sense of the scope of the invention. This description should be read to include one or at least one and the singular also includes the plural unless it is obvious that it is meant otherwise.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

After reading the specification, skilled artisans will appreciate that certain features are, for clarity, described herein in the context of separate embodiments, may also be provided in combination in a single embodiment. Conversely, various features that are, for brevity, described in the context of a single embodiment, may also be provided separately or in any subcombination. Further, references to values stated in ranges include each and every value within that range.

Additionally, the section headings herein are provided for consistency with the suggestions under 37 C.F.R. 1.77 or otherwise to provide organizational cues. These headings shall not limit or characterize the invention(s) set out in any claims that may issue from this disclosure. Specifically, a description of a technology in the "Background" is not to be construed as an admission that technology is prior art to any invention(s) in this disclosure. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of such claims shall be considered on their own merits in light of this disclosure, but should not be constrained by the headings herein.

What is claimed is:

1. A method of preparing hydrogel polymeric particles, the method comprising:
    filtering a plurality of hydrogel polymeric particles through a first filter having a pore size at a first permeate velocity to provide a first subset of hydrogel polymeric particles in the permeate and having a first particle size distribution; and
    filtering the first subset of hydrogel polymeric particles through a second filter having the pore size at a second permeate velocity to provide a second subset of hydrogel polymeric particles in the retentate derived from the first subset of hydrogel polymeric particles and having a second particle size distribution narrower than the first particle size distribution;
    wherein the average particle size of the second subset of hydrogel polymeric particles is in a range of 0.3 micrometers to 1.5 micrometers;
    wherein the first and second permeate velocities are different.

2. The method of claim 1, wherein the first permeate velocity is greater than the second permeate velocity.

3. The method of claim 1, wherein the first permeate velocity is in a range of 0.01 cm/min to 0.17 cm/min, a range of 0.02 cm/min to 0.17 cm/min, a range of 0.05 cm/min to 0.16 cm/min, a range of 0.07 to 0.15 cm/min, or a range of 0.08 cm/min to 0.15 cm/min.

4. The method of claim 1, wherein the second permeate velocity is in a range of 0.01 cm/min to 0.17 cm/min, a range of 0.02 cm/min to 0.14 cm/min, a range of 0.02 cm/min to 0.11 cm/min, a range of 0.02 cm/min to 0.085 cm/min, or a range of 0.02 cm/min to 0.075 cm/min.

5. A method of preparing polymeric particles, the method comprising:
    filtering a plurality of polymeric particles through a first filter having a first pore size at a first permeate velocity to provide a first subset of polymeric particles having a first average particle size; and
    filtering the first subset of polymeric particles through a second filter having a second pore size at a second permeate velocity to provide a second subset of polymeric particles having a second average particle size greater than the first average particle size;
    wherein the second average particle size is in a range of 0.3 micrometers to 1.5 micrometers;
    wherein the first and second pore sizes are at least the second average particle size; and
    wherein the first and second pore sizes are approximately equal.

6. The method of claim 5, wherein the first permeate velocity is greater than the second permeate velocity.

7. The method of claim 5, wherein the first permeate velocity is in a range of 0.01 cm/min to 0.17 cm/min, a range of 0.02 cm/min to 0.17 cm/min, a range of 0.05 cm/min to 0.16 cm/min, a range of 0.07 to 0.15 cm/min, or a range of 0.08 cm/min to 0.15 cm/min.

8. The method of claim 5, wherein the second permeate velocity is in a range of 0.01 cm/min to 0.17 cm/min, a range of 0.02 cm/min to 0.14 cm/min, a range of 0.02 cm/min to 0.11 cm/min, a range of 0.02 cm/min to 0.085 cm/min, or a range of 0.02 cm/min to 0.075 cm/min.

9. The method of claim 7, wherein the plurality of polymeric particles are hydrogel particles.

* * * * *